United States Patent [19]

Schmitz et al.

[11] Patent Number: 5,210,028
[45] Date of Patent: May 11, 1993

[54] PROCESS FOR THE PRODUCTION OF UNFUSED IGF-II PROTEIN IN *E. COLI*

[75] Inventors: Albert Schmitz, Basel; Walter Märki, Möhlin, both of Switzerland

[73] Assignee: Ciba-Geigy Corporation, Ardsley, N.Y.

[21] Appl. No.: 616,470

[22] Filed: Nov. 21, 1990

[30] Foreign Application Priority Data

Nov. 29, 1989 [GB] United Kingdom ............... 8927008

[51] Int. Cl.$^5$ .................. C12N 15/17; C12N 15/18; C12N 1/21
[52] U.S. Cl. .................. 435/69.4; 435/69.1; 435/252.33; 435/320.1; 935/38; 530/303; 530/324
[58] Field of Search ............. 435/252.3, 252.33, 255, 435/320.1, 172.3, 69.1, 69.4; 536/27

[56] References Cited

U.S. PATENT DOCUMENTS

| | | | |
|---|---|---|---|
| 2,586,170 | 2/1952 | Lawrenz | 43/17.2 |
| 2,807,905 | 10/1957 | Ford | 43/17.2 |
| 2,807,906 | 10/1957 | Mun | 43/17.2 |
| 2,809,460 | 10/1957 | Taylor | 43/17.2 |
| 3,144,728 | 8/1964 | Stevens | 43/17.2 |
| 3,156,064 | 11/1964 | Czirr | 43/17.2 |
| 4,408,411 | 10/1983 | Skarnells | 43/17.2 |
| 4,536,984 | 8/1985 | Kowal | 43/17.2 |
| 4,758,512 | 7/1988 | Goldberg | 435/68 |

FOREIGN PATENT DOCUMENTS

| | | |
|---|---|---|
| 0123228 | 9/1984 | European Pat. Off. . |
| 0176341 | 3/1986 | European Pat. Off. . |
| 0193112 | 12/1986 | European Pat. Off. . |
| 0230869 | 11/1987 | European Pat. Off. . |
| 0289314 | 6/1988 | European Pat. Off. . |
| WO85/00831 | 4/1985 | PCT Int'l Appl. . |
| WO86/00619 | 3/1986 | PCT Int'l Appl. . |
| WO89/03423 | 2/1989 | PCT Int'l Appl. . |

OTHER PUBLICATIONS

Hammarberg, B. et al., *PNAS*, 86:4367-4371, Jun. 1989.
Rhee, H. et al., *Journal of Biotechnology*, 13:293-304, 1990.
Prokop, A. et al. (ed.), *Recombinant DNA Technology and Applications*, McGraw-Hill, Inc., New York, 1991, pp. 285, 290-291, 299-305.
Hummel, M. et al., *Eur. J. Biochem.*, 180:555-561, 1989.
Rinderknecht and Humbel, FEBS letters, 89:283-286 (1978).
Smith et al., *J. Biol. Chem.*, 264:9314-9321 (1989).
Buell et al., *Nucleic Acids Res.*, 13:1923-1938 (1985).
Amann et al., *Gene*, 69:301-315 (1988).

*Primary Examiner*—Robert J. Hill, Jr.
*Assistant Examiner*—Marianne Porta Allen
*Attorney, Agent, or Firm*—Joann Villamizer; Steven R. Lazar; W. Murray Spruill

[57] ABSTRACT

A process for the preparation of a recombinant IGF-II (rIGF-II) without a covalently attached foreign protein moiety and without N-terminal attached methionine or a derivative of methionine or of a salt of said IGF-II, rIGF-II produced by said method, hybrid vectors comprising DNA encoding said rIGF-II, hosts transformed with said vectors, and a process for the isolation of said rIGF-II from the host cell and refolding it into a biologically active form.

15 Claims, 7 Drawing Sheets

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
    (A) LENGTH: 67 amino acids
    (B) TYPE: amino acid
    (D) TOPOLOGY: linear (ii) MOLECULE TYPE: protein (iii) HYPOTHETICAL: N (iv) ANTI-SENSE: N (vi) ORIGINAL SOURCE:
    (A) ORGANISM: Human IGF-II (xi) SEQUENCE DESCRIPTION: SEQ ID NO:1:

```
Ala Tyr Arg Pro Ser Glu Thr Leu Cys Gly Gly Glu Leu Val Asp Thr
 1               5                  10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
            35                  40                  45

Arg Ser Cys Asp Leu Ala Leu Leu Glu Thr Tyr Cys Ala Thr Pro Ala
        50                  55                  60

Lys Ser Glu
 65
```

(2) INFORMATION FOR SEQ ID NO:2:

(i) SEQUENCE CHARACTERISTICS:
    (A) LENGTH: 216 base pairs
    (B) TYPE: nucleic acid
    (C) STRANDEDNESS: double
    (D) TOPOLOGY: linear (ii) MOLECULE TYPE: cDNA (iii) HYPOTHETICAL: N (iv) ANTI-SENSE: N (vi) ORIGINAL SOURCE:
    (A) ORGANISM: Synthetic Human IGF-II DNA Sequence; E.coli pref
    (B) STRAIN: pBB8/IGF-II (xi) SEQUENCE DESCRIPTION: SEQ ID NO:2:

```
CATATGGCAT ACCGCCCGAG CGAGACCCTG TGCGGTGGCG AGCTCGTAGA CACTCTGCAG    60

TTCGTTTGTG GTGACCGTGG CTTCTACTTC TCTCGTCCTG CTAGCCGTGT ATCTCGCCGT   120

TCTAGAGGCA TCGTTGAAGA GTGCTGTTTC CGCAGCTGTG ATCTGGCACT GCTCGAAACT   180
```

-continued

TACTGCGCAA CTCCAGCAAA ATCCGAATAA GGATCC 216

( 2 ) INFORMATION FOR SEQ ID NO:3:

( i ) SEQUENCE CHARACTERISTICS:
        ( A ) LENGTH: 233 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: N ( i v ) ANTI-SENSE: N ( v i ) ORIGINAL SOURCE:
        ( A ) ORGANISM: Synthetic huIGF-II DNA sequence; yeast preferred
        ( B ) STRAIN: pIGF-II/3

( x i ) SEQUENCE DESCRIPTION: SEQ ID NO:3:

GAATTCGACG CTTATGGCTT ACAGACCATC CGAAACCTTG TGTGGTGGTG AATTGGTCGA 60

CACCTTGCAA TTCGTTTGTG GTGACAGAGG TTTCTACTTC TCCAGACCAG CTTCCAGAGT 120

TTCTAGAAGA TCCAGAGGTA TCGTTGAAGA ATGTTGTTTC AGATCTTGTG ACTTGGCTTT 180

GTTGGAAACC TACTGTGCTA CCCCAGCTAA GTCTGAATGA ATGCGTCGAA TTC 233

( 2 ) INFORMATION FOR SEQ ID NO:4:

( i ) SEQUENCE CHARACTERISTICS:
        ( A ) LENGTH: 150 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: N ( i v ) ANTI-SENSE: N ( v i ) ORIGINAL SOURCE:
        ( A ) ORGANISM: ner gene ribosomal binding site of phage Mu
        ( B ) STRAIN: pPLMu ( x i ) SEQUENCE DESCRIPTION: SEQ ID NO:4:

GAATTCTTAC ACTTAGTTAA ATTGCTAACT TTATAGATTA CAAAACTTAG GAGGGTTTTT 60

ACCATGGTTA CGAATTCCCG GGGATCCGTC GACCTGCAGC CAAGCTTGGC TGCCTCGCGC 120

GTTTCGGTGA TGACGGTGAA AACCTCTGAC 150

PROCESS FOR THE PRODUCTION OF UNFUSED IGF-II PROTEIN IN E. COLI

The invention relates to the field of recombinant DNA technology and concerns a process for the preparation of a recombinant IGF-II (rIGF-II) without a covalently attached foreign protein moiety and without N-terminal attached methionine or a derivative of methionine, or of a salt of said rIGF-II, rIGF-II produced by said method, hybrid vectors comprising DNA encoding said rIGF-II, hosts transformed with said vectors, and a process for the isolation of said rIGF-II from the host cell and refolding it into a biologically active form.

Insulin-like growth factor II (IGF-II) is a member of the IGF-family of polypeptide growth factors with insulin-like activities. The IGF-Family comprises insulin, relaxin, IGF-I, IGF-II, and the β-subunit of the 7s nerve growth factor (Blundell and Humbel, Nature 287: 781–787, 1980; Froesch and Zapf, Diabetologica 28: 485–493, 1985; Froesch et al., Ann. Rev. Physiol. 47: 443–467, 1985).

The physiological function of the serum protein IGF-II is not yet fully understood. It is known, however, that IGF-II stimulates thymidine incorporation by activated T cells (Brown et al., J. Receptor Res. 5: 297, 1985), enhances erythroid colony formation by bone marrow cells (Dainniak and Kreczuko, J. Clin. Invest. 76: 1237, 1985) and may be involved in transforming growth factor-β induced soft agar growth of normal rat kidney cells (Massague et al., J. Biol. Chem. 260: 455, 1985). IGF-II seems to be involved in the regulation of embryonal development and to be regulated by a placental factor (Scheonle et al., Nature 296, 252–253, 1982; Adams et al., Nature 302: 150–153, 1986). The European patent application EP-A-0 289 314 discloses that IGF-II is the same as skeletal growth factor (SGF), which is mitogenic for bone cells (Farley et al., Biochemistry 21: 3509, 1982) and has been implicated in the stimulation of collagen synthesis (Linkhart et al., J. Cell. Physiol. 128: 307, 1986). IGF-II can be used for the treatment of bone disorders.

Mature IGF-II in the serum is derived from the cellular translational product prepro-IGF-II. Prepro-IGF-II is proteolytically cleaved to pro-IGF-II during transmembrane transport which is then further processed to mature IGF-II.

IGF-II may be found in a wide range of organisms including mammalia and birds. Different species of animals may have different IGF-II molecules and in a particular species or even in a particular individuum several variants of IGF-II may be synthesized. Rinderknecht and Humble described the amino acid sequence of a human IGF-II (huIGF-II) in FEBS Lett. 89: 283–286, 1978. The protein consists of a single chain which has 67 amino acids. The primary structure of said protein is given in the sequence listing under SEQ ID No. 1.

A rat equivalent of huIGF-II (ratIGF-II) was isolated from the conditioned medium of the rat cell line BRL-3A (Dulate and Shing, J. Cell. Physiol. 90: 127–138, 1976) and sequenced (Marquardt et al., J. Biol. Chem. 256: 6859–6865, 1981). U.S. Pat. No. 4,783,542 discloses the amino acid sequence of bovine IGF-II (boIGF-II). Preparation of IGF-II from chicken bone is disclosed in EP 0 289 314.

Jansen et al. (FEBS Lett. 179: 243–264, 1985) disclose a variant of huIGF-II which has the tetrapeptide arginine-leucine-proline-glycine instead of serine in position 29. Another variant form of huIGF-II, which has the tripeptide cysteine-glycine-aspartate instead of serine in position 33 is disclosed by Zumstein et al. in Proc. Natl. Acad. Sci. U.S.A. 82: 3169–72 (1985). A further variant of IGF-II lacks the N-terminal alanine so that the amino acid sequence starts with tyrosine at the N-terminus (des-Ala-IGF-II). Des-Ala-IGF-II was identified both in human and rat (Rinderknecht and Humbel, FEBS Lett. 89: 283–286, 1978; Marquardt et al., J. Biol. Chem. 256: 6859–6863, 1981).

The huIGF-II gene encoding the prepro-form of huIGF-II consists of at least five exons and 4 introns and spans a region of about 16 kbp on chromosome 11 (de Pagter-Holthuizen et al., FEBS Lett. 195: 179–184, 1986).

As described by Jansen et al. (FEBS Lett. 179: 243–264, 1985) two closly related but distinct types of cDNA corresponding to two different mRNA transcripts were isolated from the same human liver cDNA library. One cDNA type encodes the huIGF-II having the amino acid sequence having the SEQ ID No. 1. The second cDNA type encodes the above mentioned variant of huIGF-II which has the tetrapeptide arginine-leucine-proline-glycine glycine instead of serine in position 29. It has been discovered that the different mRNA transcripts are predominantly expressed in specific tissues. cDNAs encoding prepro- or mature IGF-II are disclosed by e.g. Jansen et al. (FEBS Lett. 179: 283–286, 1985), de Pagter-Holthuizen et al. (FEBS. Lett. 195: 179–184, 1986), PCT/WO 8600619, U.S. Pat. No. 4,783,524, Jansen et al. (Nature 306: 609–611, 1983), and in EP-A-0 193 112.

Whether variant forms of IGF-II are the products of allelic IGF-II genes with a slightly modified encoding sequence or whether variants are formed by alternate splicing of the primary transcript of a single IGF-II gene is not yet clear (de Pagter-Holthuizen et al., above).

To provide large amount of IGF-II protein is of scientific and clinical interest. Methods are known to produce IGF-II from human serum (Rinderknecht and Humbel, FEBS Lett. 89: 283–286, 1978), bone (PCT/WO 8600619), or conditioned nutrient medium of cell culture (Dulak and Sling, J. Cell. Physiol. 90: 127–138, 1976). By means of these methods, however, only limited amounts of IGF-II can be produced. Availability of the amino acid sequence and of cDNA made it possible to produce larger amounts of IGF-II or variants thereof, e.g. an [$Arg^{54}Arg^{55}$]-variant (PCT/WO 85/00831), by recombinant gene technology. Hereinafter, IGF-II produced by recombinant gene technology is referred to as rIGF-II.

The genetic code is degenerate, that means many amino acids are specified by more than one codon. For example, serine is encoded by the desoxyribonucleotide TCT, TCC, TCA, TCG, AGT, and AGC. Thus, it is possible to synthesize genes with different DNA sequences which encode the same amino acid sequence. Different synthetic genes which encode human IGF-II are disclosed by e.g. Furman et al., BIO/TECHNOLOGY 5: 1047–1051 (1987), in PCT/WO 8903423, PCT/WO 8500831, EP 0 176 341 and EP 0 123 228.

Expression in E. coli of polypeptides comprising IGF-II amino acid sequences is disclosed e.g. in the European patent applications EP-0 230 860, and EP-0 176 341. Up to now only rIGF-II-fusion proteins were produced in E. coli. These fusion proteins have the disadvantage that they must be cleaved, either enzymatically or chemically, and then rIGF-II must be separated from the other cleavage products. Thus, to produce rIGF-II-fusion proteins is disadvantageous with respect to the number of steps which must be performed to obtain purified rIGF-II and to the possibility of modification of the protein during chemical cleavage.

Proteins expressed in E. coli often contain a methionine or a derivative of methionine, for example N-formyl-methionine, attached to the N-terminus because in E. coli cells the N-terminal methionine which is the starter amino acid in protein biosynthesis is often not cleaved from the polypeptide chain.

Production in E. coli of heterologous proteins being not fused to a bacterial or bacteriophage protein moiety may be a problem with respect to the susceptibility of the heterologous protein to proteolytic degradation by the host cell. For this reason host strains were developed which are defective in proteases which degrade heterologous proteins. Such a host strain is, for example, E. coli LC 137, which is defective in the protease gen lon and in the htpR gene, the product of which regulates heat shock induced protein synthesis.

Foreign proteins that contain disulfide bonds are produced in microorganisms often in an insoluble form that lacks the correct disulfide bonds, is reduced and has a non-native conformation. In a number of E. coli strains, for example in E. coli LC 137, such insoluble foreign proteins are stored as inclusion bodies in the cytoplasm. The incorrectly folded proteins are essentially inactive (Smith et ala., Science 229: 1219, 1985).

On cell breakage in the absence of reducing agents in the breakage buffer the incorrectly folded proteins may have incorrect disulfide pairing, probably due to oxidation of sulfhydryl groups in the wrongly folded protein by oxygen of the air.

Attempts have been made to restore the biological activity of incorrectly folded proteins by refolding them into the naturally occuring mature form. The refolding techniques in principle comprise isolation of inclusion bodies from the cells, solubilization of inclusion bodies and denaturing the incorrectly folded proteins, eventually accompanied by reducing incorrectly formed disulphide bonds and allowing the protein to form the mature renatured form and to oxidize sulfhydryl groups of the protein so that the correct intramolecular disulphide bridges which stabilize the mature refolded protein may be formed.

Refolding procedures comprising reduction, solubilization and reoxidation are known in the art (K. J. Doege and J. H. Fessler, J. Biol. Chem. 261, 1986, 8924–8935; J. G. L. Petersen and K. J. Dorrington, J. Biol. Chem. 249, 1974, 5633–5641; V. P. Saxena and D. B. Wetlaufer, Biochemistry, 9, 1970, 5015–5022; EP 219 874). For each particular protein, however, the exact conditions for the refolding by reduction, solubilization and reoxidation have to be developed and are not predictable. Not for all proteins attempts have been successful to refold incorrectly folded proteins into a biologically active, naturally occuring form. In Smith et al. (J. Biol. Chem. 264: 9314–9321, 1989) refolding of a recombinant human IGF-II which was prepared by cleaving a fusion protein expressed in E. coli is described. However, in the refolding process a polymerized IGF-II and two structural isomeric monomers were formed.

It is the object of the present invention to produce in E. coli large amounts of rIGF-II without a covalently attached foreign protein moiety and without N-terminal attached methionine or a derivative of methionine.

A further object of the invention is to provide biological active rIGF-II by refolding of the rIGF-II produced in E. coli into a biologically active form.

DETAILED DESCRIPTION OF THE INVENTION

Figure 1:
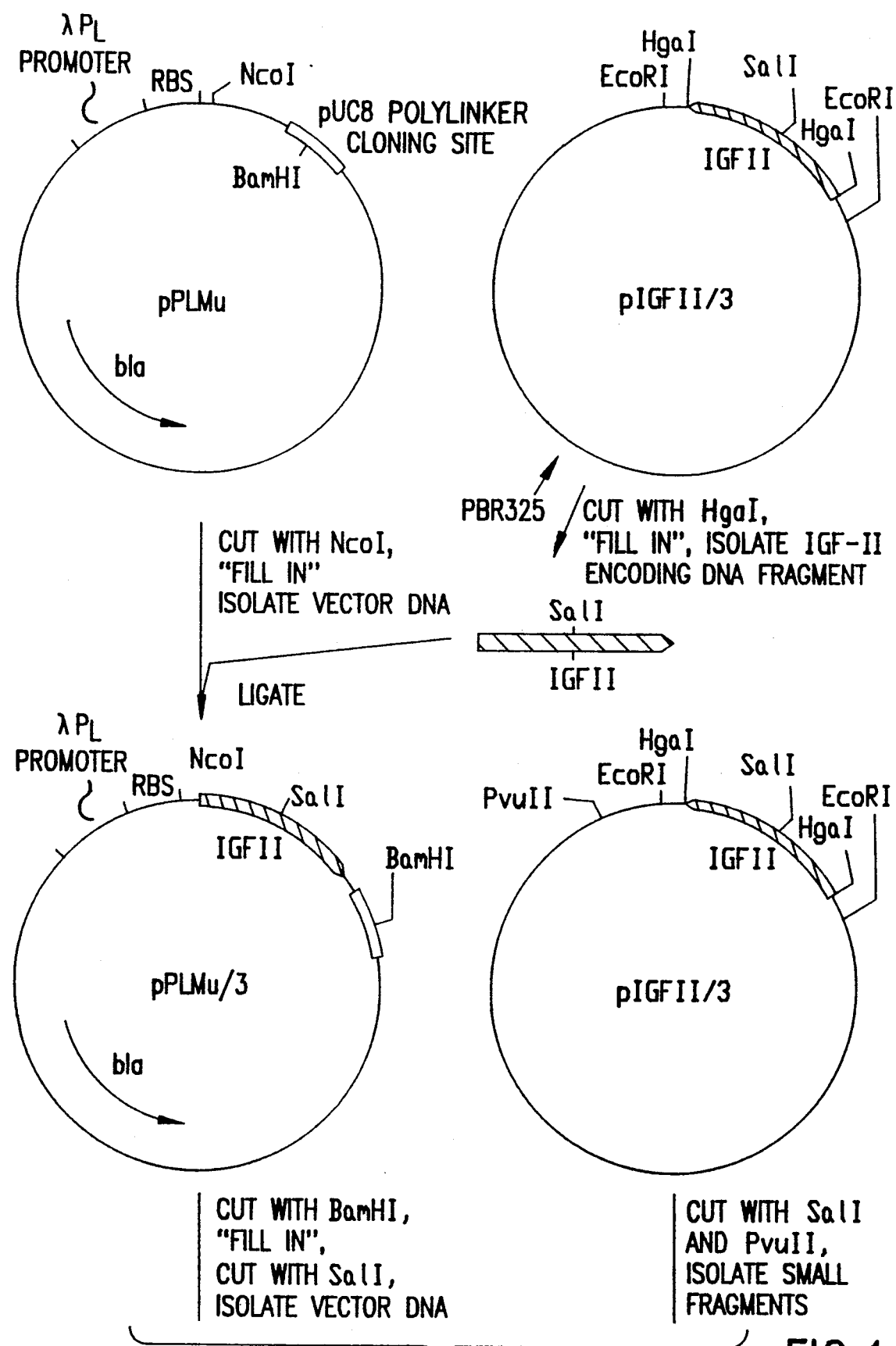
Figure 1:
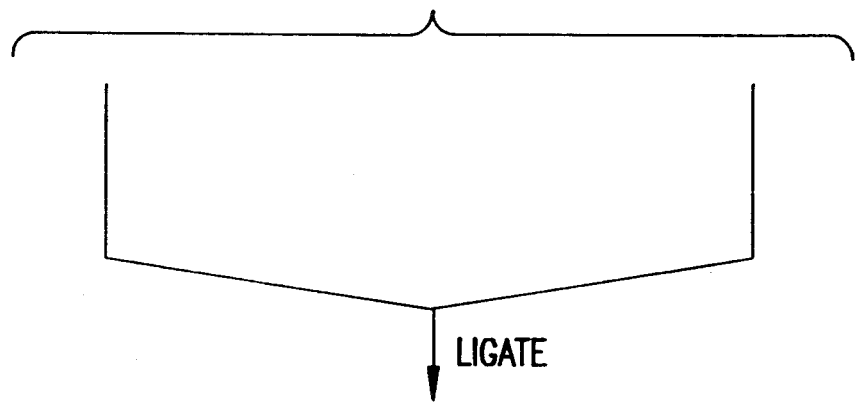
Figure 1:
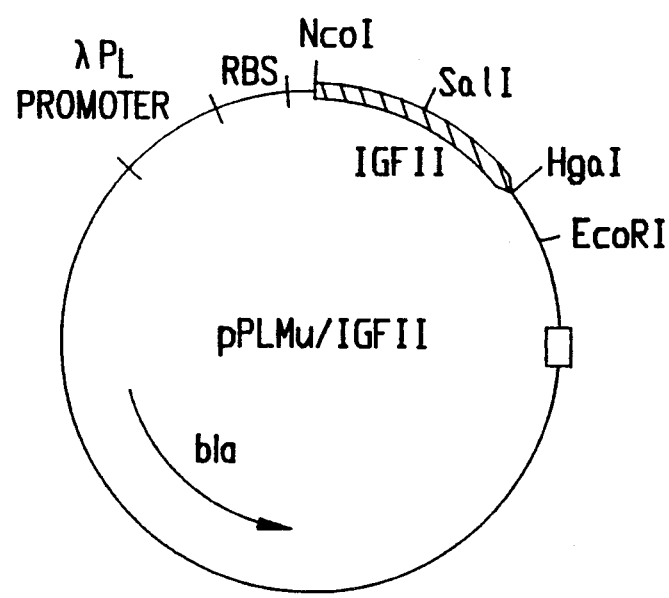

The invention concerns a process for the production of a rIGF-II without a covalently attached foreign protein moiety and without N-terminal attached methionine or a derivative of methionine comprising
1) transformation of a suitable microbial host strain with a hybrid vector comprising an expression cassette consisting of a promoter operably linked to a first DNA sequence containing a ribosomal binding site and encoding the amino acid methionine linked in the proper reading frame to a second DNA sequence encoding an IGF-II.
2) culturing said transformed host strain.

A rIGF-II is a polypeptide consisting substantially of amino acid sequences of naturally occuring mature IGF-II and having one or more determinable biological IGF-II functions.

Included within the scope of rIGF-II are all variants and fragments thereof with IGF-II activity. Variants are intended to include naturally occuring variants found in different species, e.g. in different mammals, e.g. in mouse, rat, human, bovine, or in birds, e.g. in chicken, or found within a particular species, e.g. a variant which has the tetrapeptide arginine-leucine-proline-glycine instead of serine in position 29 of the amino acid sequence of human IGF-II (huIGF-II) shown in the sequence listing under sequence Identification No. (SEQ ID NO.) 1, a variant which has the tripeptide cysteine-glycine-aspartate instead of serine in position 33 of the amino acid sequence with the SEQ ID NO. 1, or a variant which lacks the N-terminal amino acid. Variants are also intended to include rIGF-II forms produced from DNA which was mutated in vitro in order to change the amino acid sequence of the encoded protein. Such variants have an amino acid sequence in which e.g. 1 up to about 10 amino acids are deleted or exchanged with one or more other amino acids.

The preferred rIGF-II is the huIGF-II having the amino acid sequence with the SEQ ID No. 1.

DNA encoding an IGF-II can be manufactured by methods known in the art and consists of cDNA isolated from a mammalian cDNA library, e.g. from human, mouse, rat or bovine, or an avian cDNA library, e.g. from chicken. The cDNA library may be derived from cells from different tissues, e.g. liver cells or bone cells. DNA encoding IGF-II also consists of genomic DNA, e.g. isolated from a mammalian genomic DNA library, e.g. from human, mouse, rat or bovine cells, or from an avian genomic DNA library, e.g. from chicken cells. DNA encoding IGF-II consists further of chemically synthesized DNA having the DNA sequence either of a naturally occuring IGF-II encoding DNA or of a mutant thereof. A mutant of the naturally occuring DNA is encoding a naturally occuring IGF-II or a variant form thereof having IGF-II activity and/or having an amino acid sequence in which e.g. 1 up to about 10 amino acids are deleted or exchanged with one or more other amino acids. A mutant DNA encoding a naturally occuring IGF-II is also intended to be a silent mutant wherein one or more nucleotides are replaced by other nucleotides, whereby the new codons code for the same amino acid(s). Such a mutant DNA sequence is also a degenerated DNA sequence. Degenerated DNA sequences are degenerated within the meaning of the genetic code in that an unlimited number of nucleotides are replaced by other nucleotides without changing the amino acid sequence for which they code. Such degenerated DNA sequences may be useful because of their different restriction sites and/or of their frequency of particular codons which are preferred by a particular host to obtain optimal expression of rIGF-II. Preferred examples of such DNA sequences have the *E. coli* preferred codon usage and the yeast preferred codon usage, respectively, and are shown in the sequence listing under SEQ ID NO. 2 and 3, respectively.

Suitable microbial host strains are, for example, strains of *E. coli*. Preferred is the use of *E. coli* strains defective in protease genes, e.g. in the lon protease gene, and genes involved in the regulation of heat shock induced protein synthesis, e.g. in the htpR gene (U.S. Pat. No. 4,758,512; Buell, G. et al., Nucleic Acids Res. 13: 1923-1938, 1985).

A suitable vector for the production of a hybrid vector according to the invention is a vector which is operable in the microbial host cell.

Suitable hybrid vectors contain a complete replicon and a marker gene, which renders possible the selection and identification of the microorganism transformed by the expression plasmids by means of a phenotype feature. Suitable marker genes impart to the microorganism, for example, resistance to heavy metals, antibiotics such as ampicillin or tetracyclin, and the like.

Examples of vectors that are suitable for the expression of the IGF-II gene in an *E. coli* strain are bacteriophages, for example derivatives of the bacteriophage λ, or plasmids, for example pMB9, pSF2124, pBR317, pBR322 or pPLMu. Preferred is pPLMu, which is disclosed in Buell et al., Nucl. Acids Res. 13: 1923-1938 (1985). Preferred hybrid vectors comprising a DNA sequence encoding IGF-II are pPLMu/BB and pPLMu/IGF-II.

Several promoters can be used for regulating the expression of the IGF-II gene in *E. coli*. Especially useful are promoters of strongly expressed genes which can be tightly regulated. Suitable promoters are e.g. the lac, tac, trp and lpp promoters, furthermore the phage λN or the phage $\lambda P_L$ promoter. A preferred promoter for use in *E. coli* is a tightly regulated promoter, e.g. the $\lambda P_L$, $\lambda P_R$, lac or trp promoter. Most preferred is the $\lambda P_L$ promoter. It is comprises in e.g. vector pPLMu.

A ribosomal binding site (Shine-Dalgarno Sequence) is either naturally linked to the promoter used or may be located on a short nucleotide sequence which may be covalently linked 5' to the coding region of IGF-II, Preferred is the phage Mu ner gene ribosomal binding site which is comprised in the DNA sequence shown under SEQ ID No. 4.

The transformed microbial host strains are cultured in a liquid medium containing assimilatable sources of carbon, nitrogen and inorganic salts, applying methods known in the art.

In a preferred embodiment of the invention the promoter comprised in the expression cassette of the hybrid vector can be regulated by a regulatory protein and the production of rIGF-II in the transformed host cell can be induced. The DNA sequence encoding a protein regulating the promoter comprised in the expression cassette of the hybrid vector may be comprised either in the genome of the host strain or by an additional plasmid vector the host strain may be transformed with or in the hybrid vector of the invention. The selection of a suitable DNA sequence encoding a protein regulating the promoter comprised in the expression cassette of the hybrid vector depends on the promoter. A DNA sequence encoding a protein regulating the promoter is, for example, a gene encoding a repressor protein, e.g. trpR, lacI, λcro, or λcI, or a temperature sensitive mutant thereof.

The conditions for the induction of the production of rIGF-II depend on the promoter and on the DNA sequence encoding a protein regulating said promoter. If the thermolabil $\lambda CI_{857}$ repressor is used, a heat induction is performed at about 42° C. for about 1 up to about 10 h.

When the amount of rIGF-II in the host cell has reached a satisfying level, the culture is interrupted and the polypeptide can be isolated. rIGF-II may be deposited in the cell in inclusion bodies.

A preferred process for the production of rIGF-II comprises culturing of *E. coli* LC137 transformed with the plasmid $pcI_{857}$ encoding the thermolabil $\lambda CI_{857}$ repressor and with a hybrid vector consisting of pPLMu comprising an expression cassette consisting of the $\lambda P_L$ promoter operably linked to a first DNA sequence containing the phage Mu ner gene ribosome binding site the sequence of which is given under SEQ ID No. 4 and encoding the amino acid methionine linked in the proper reading frame to a DNA with the SEQ ID NO. 2 or 3, encoding huIGF-II, and inducing expression of rIGF-II by heat induction at about 42° C. In particular preferred is the use of *E. coli* LC 137 transformed with plasmid $pcI_{857}$ and with plasmid pPLMu/IGF-II or with pPLMu/BB.

The invention concerns also a process for the isolation of rIGF-II from the host cells and for refolding rIGF-II into a biologically active form by reducing the disulfide bonds and solubilizing the reduced polypeptide under denaturing conditions, allowing the denatured polypeptide to fold into naturally occuring form, and reoxidizing the sulfhydryl groups to form disulfide bonds. Said process comprises the steps a) isolating rIGF-II produced by the host cells.

b) dissolving rIGF-II in a suitable solution, c) refolding rIGF-II into a biologically active form by dialyzing the rIGF-II solution obtained in step b) against folding buffer and incubating the rIGF-II in folding buffer under oxygen free conditions in the presence of an oxidizing substance to allow slowly oxidizing or reduced sulfhydryl radicals to intramolecular disulfide bonds so that rIGF-II is refolded into a biologically active form.

d) if desired, converting an obtained polypeptide having free carboxy and/or amino groups into a salt or converting a salt obtained into the free compound.

In a preferred embodiment of the invention rIGF-II which is produced in *E. coli* according to the method described hereinbefore, is isolated from the host cell and refolded.

rIGF-II is isolated from the cells in conventional manner.

Methods for breaking host cells and isolating inclusion bodies are well known in the art. Cells may be broken, for example, by sonification with ultra-sound, alternating freezing, e.g. in liquid nitrogen, and thawing, or by mechanical forces, such as sharing forces, for example by french-pressing. Inclusion bodies may be sedimented by centrifugation of the suspension of broken cells e.g. for about 10-30 min at about 4,000 g up to about 15,000 g after breaking the cells.

A suitable solution for dissolving rIGF-II comprises a reducing agent and a chaotrop in a concentration sufficient for unfolding rIGF-II and, if required, a proteinase inhibitor.

Reducing agents useful in the present invention are agents reducing disulfide groups to sulfhydryl groups, for example reagents containing mercapto groups, such as dithiothreitol (DTT), dithioerythrol (DTE), mercaptomethanol, mercaptoethanol, cystein or reduced glutathion (GSH).

Chaotropes useful for said unfolding are for example urea, guanidine-HCl, arginine, or also salts, such as potassium thiocyanate or water soluble calcium, salts, e.g. $CaCl_2$.

Preferred is urea and in particular guanidine-HCl.

The concentration of urea or guanidine-HCl sufficient for unfolding rIGF-II is from about 7M to about 9M.

Proteinase inhibitors useful in the present process are, for example, benzamidine, ethylene diamino tetraacetic acid, phenylmethylsulfonylfluoride (PMSF), diisopropylfluorophosphate (DIFP), tosylphenylaalanylchloromethylketone (TPCK), tosylleucylchloromethylketone (TLCK), o-phenanthroline, microbial protease inhibitors such as pepstatin, leupeptine or antipain or soybeam trypsin inhibitor (SBTI) and the like.

Another suitable solution for dissolving rIGF-II is an aqueous solution comprising a carboxylic acid, for example, $C_2$-$C_4$ carboxylic acid. A preferred carboxylic acid is acetic acid. The concentration of said solution of a carboxylic acid is from about 0.1% (v/v) to about 70% (v/v) of the $C_2$-$C_4$ carboxylic acid. Preferred acetic acid concentration is from about 50% (v/v) to about 70% (v/v). If the carboxylic acid concentration, e.g. acetic acid concentration, is low, e.g. about 0.1% (v/v), pH must be adjusted to about pH 2 to 4, preferentially to pH 3. pH may be adjusted, for example, with a hydrohalic acid, e.g. HCl.

Dialyzing a solution of rIGF-II obtained in step b) against folding buffer may be performed at a temperature of about 0° C. to about 10° C., preferentially at about 4° C. After dialysis, the rIGF-II may be incubated in the folding buffer for about 18 h to about 96 h at a temperature of about 4° C. to about 35° C. in a concentration from about 10 µg/ml up to about 400 µg/ml, preferentially about 100 µg/ml.

A folding buffer useful in the present process comprises a chaotrop, e.g. guanidine-HCl or urea, in a concentration from about 1M to about 2.5M, preferentially in a concentration of about 2M.

If the rIGF-II solution is contaminated with protease, the folding buffer additionally may comprise a proteinase inhibitor as defined hereinbefore.

Oxygen free conditions may be obtained by degassing with an inert gas, e.g. nitrogen or a noble gas, e.g. helium or argon.

A folding buffer useful in the present invention also comprises an oxidizing substance.

Oxidizing substances according to the present invention are substances or redox pairs of substances providing the solution with a redox potential lower than the sulfhydryl/disulfide redox pair so that the sulfhydryl groups of proteins are oxidized to disulfide groups.

Oxidizing substances or redox pairs are e.g. (oxidized) glutathione (GSSG) or a mixture of reduced and oxidized glutathione, cystine or a mixture of cysteine and cystine, and the like. The concentration of the substances or the ratio of the members of a redox pair is elected so that the redox potential of the folding buffer is low enough to oxidize the sulfhydryl groups of rIGF-II.

rIGF-II may be further purified. Purification steps may be performed prior to or after refolding of rIGF-II.

Methods suitable for further purification of rIGF-II prior to or after refolding are well known, e.g. standard chromatographic methods, such as gel filtration, ion exchange chromatography, chromatography on DEAE cellulose, immunoaffinity, or HPLC. A method for further purification of rIGF-II prior to refolding is, for example, gel filtration on a gel filtration column, e.g. a Sephacryl S-200 column, which is equilibrated and eluted with a solution suitable for dissolving rIGF-II defined hereinbefore.

Refolded rIGF-II is obtained from the folding buffer in a conventional manner, for example by salting out, e.g., with ammonium sulfate, ammonium chloride, sodium chloride, or by concentrating the protein solution, and by evaporation or lyophilization.

Depending on the method employed, refolded rIGF-II is obtained in known manner in free form or as its salts. As it contains free amino groups in several amino acid residues, the compound of the invention can be obtained in the form of an acid addition salt. Suitable acid addition salts are in particular pharmacologically acceptable salts with conventional therapeutically acceptable acids. Representative inorganic acids are hydrohalic acids (such as hydrochloric acid), and also sulfuric acid, phosphoric acid and pyrophosphoric acid. Representative organic acids are in particular arene-sulfone acids (such as benzene-sulfonic or p-toluenesulfonic acid), or lower alkanesulfonic acids (such as methane-sulfonic acid), as well as carboxylic acids such as acetic acid, lactic acid, palmitic acid, stearic acid, malic acid, tartaric acid, ascorbic acid and citric acid. As, however, the compound according to the invention also contains free carboxyl groups in several amino acid residues, which carboxyl groups impart acidic character to the entire peptide, it can also be obtained in the form of a salt with inorganic or organic bases, e.g. sodium, potassium, calcium or magnesium salts, or also ammonium salts derived from ammonia or a pharmacologically acceptable organic nitrogen-containing base. However, as it contains at the same time free carboxy groups and free amino groups, it can also be obtained in the form of an inner salt. Production of pharmacologically acceptable salts is preferred.

A pharmacologically acceptable salt can be obtained from the free compounds by reaction with acids, e.g. with those acids which form the above-mentioned salts, and by evaporation or lyophilisation, or by adjusting the pH to a suitable neutral point, and by evaporation or lyophilization.

Another embodiment of the invention is a hybrid vector comprising an expression cassette consisting of a promoter operably linked to a first DNA sequence containing a ribosomal binding site and encoding the amino acid methionine linked in the proper reading frame to a second DNA sequence coding for IGF-II. Preferred is a hybrid vector comprising the DNA sequence with SEQ ID NO. 2 or 3. Most preferred are pPLMu/BB and pPLMu/IGFII.

The hybrid vectors according to the invention can be prepared by methods known in the art, for example by linking the expression cassette consisting of a promoter operably linked to a first DNA sequence optionally encoding a ribosomal binding site and encoding the amino acid methionine linked in the proper reading frame to a second DNA sequence coding for IGF-II, or the constituents of the expression cassette to the DNA fragments containing selective genetic markers and origins of replication for the selected microbial host in the predetermined order. The preparation of said hybrid vectors is also a subject of the present invention.

The invention concerns further a microbial host transformed with a hybrid vector comprising an expression cassette consisting of a promoter operably linked to a first DNA sequence containing a ribosomal binding site and encoding the amino acid methionine linked in the proper reading frame to a seconde DNA sequence coding for IGF-II, and a method for the production thereof, comprising transforming said microbial host with said hybrid vector.

The transformed microbial host cells according to the invention can be prepared by recombinant DNA techniques comprising the steps of
transforming a microbial host strain with said hybrid vector,
and selecting transformed microbial host cells from untransformed host cells.

The transformation with the hybrid vectors according to the invention is carried out, for example, in the manner described in the literature for *E. coli* [M. Mandel et al., J. Mol. Biol. 53, 159 (1970)]. The isolation of the transformed host cells is effected advantageously from a selective nutrient medium to which there has been added, for example, the biocide against which the marker gene contained in the expression plasmid imparts resistance. If, for example, the hybrid vectors contain the amp$^R$ gene, ampicillin is accordingly added to the nutrient medium. Cells that do not contain the hybrid vector are destroyed in such a medium.

The microbial host strains are those specified above.

Most preferred transformed host strains are *E. coli* LC137 transformed with pPLMu/IGFII and pcI$_{857}$ and *E. coli* LC137 transformed with pPLMu/BB and pcI$_{857}$.

IGF-II whenever produced by a process according to the present invention is also subject of the present invention.

The present invention further concerns pharmaceutical compositions comprising IGF-II produced by a process according to the present invention or a derivative or a salt thereof. Pharmaceutical compositions are prepared in a conventional manner.

Hereinbefore and hereinafter for the description of amino acids or amino acid sequences either the three letter code or the single letter code is used which are given below:

| | | |
|---|---|---|
| A | Ala | Alanine |
| R | Arg | Arginine |
| N | Asn | Asparagine |
| D | Asp | Aspartic acid |
| C | Cys | Cysteine |
| Q | Gln | Glutamine |
| E | Glu | Glutamic acid |
| G | Gly | Glycine |
| H | His | Histidine |
| I | Ile | Isoleucine |
| L | Leu | Leucine |
| K | Lys | Lysine |
| M | Met | Methionine |
| F | Phe | Phenylalanine |
| P | Pro | Proline |
| S | Ser | Serine |

-continued

| | | |
|---|---|---|
| T | Thr | Threonine |
| W | Trp | Tryptophane |
| Y | Tyr | Tyrosine |
| V | Val | Valine |
| B | Asx | (Asn + Asp) |
| Z | Glx | (Gln + Glu) |

SHORT DESCRIPTION OF THE FIGURES

FIG. 1: Scheme of the cloning strategy for the constriction of plasmid PLMu/IGFII.

Figure 2A:
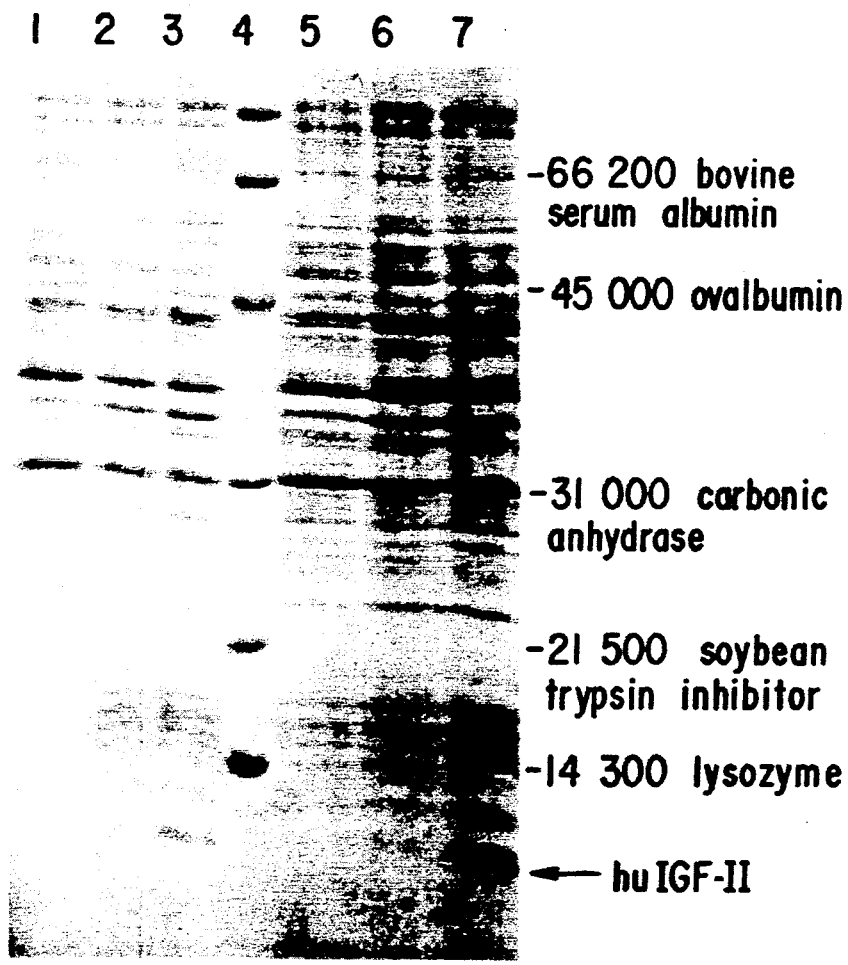

FIG. 2A: Coomassie brillant blue stained SDS-Polyacrylamide gel showing the expression of recombinant huIGF-II in *E. coli* LC137. Lane 1: 10 ul crude extract, cells not induced, Lane 2: 10 ul crude extract, cells heat-induced for 1 h, Lane 3: 10 ul crude extract, cells heat-induced for 2 h, Lane 4: Molecular weight size markers, Lane 5:20 ul crude extract, cells not induced, Lane 6: 20 ul crude extract, cells heat-induced for 1 h, Lane 7: 20 ul crude extract, cells heat-induced for 2 h.

Figure 2B:

FIG. 2B: "Western analysis" of whole cell proteins after heat induction of *E. coli* strain LC137 carrying the plasmids pPLMu/IGFII and pcI$_{857}$. Rabbit anti-huIGF-II antibodies were used. Lane 1: 10 ul of whole cell proteins, cells not induced, Lane 2: 10 ul of whole cell proteins, cell heat-induced for 1 h, Lane 3: 10 ul of whole cell proteins, cells heat-induced for 2 h, Lane 4: 10 ul of whole cell proteins, cells heat-induced for 3 h, Lane 5: purified recombinant huIGF-I standard.

Figure 3:
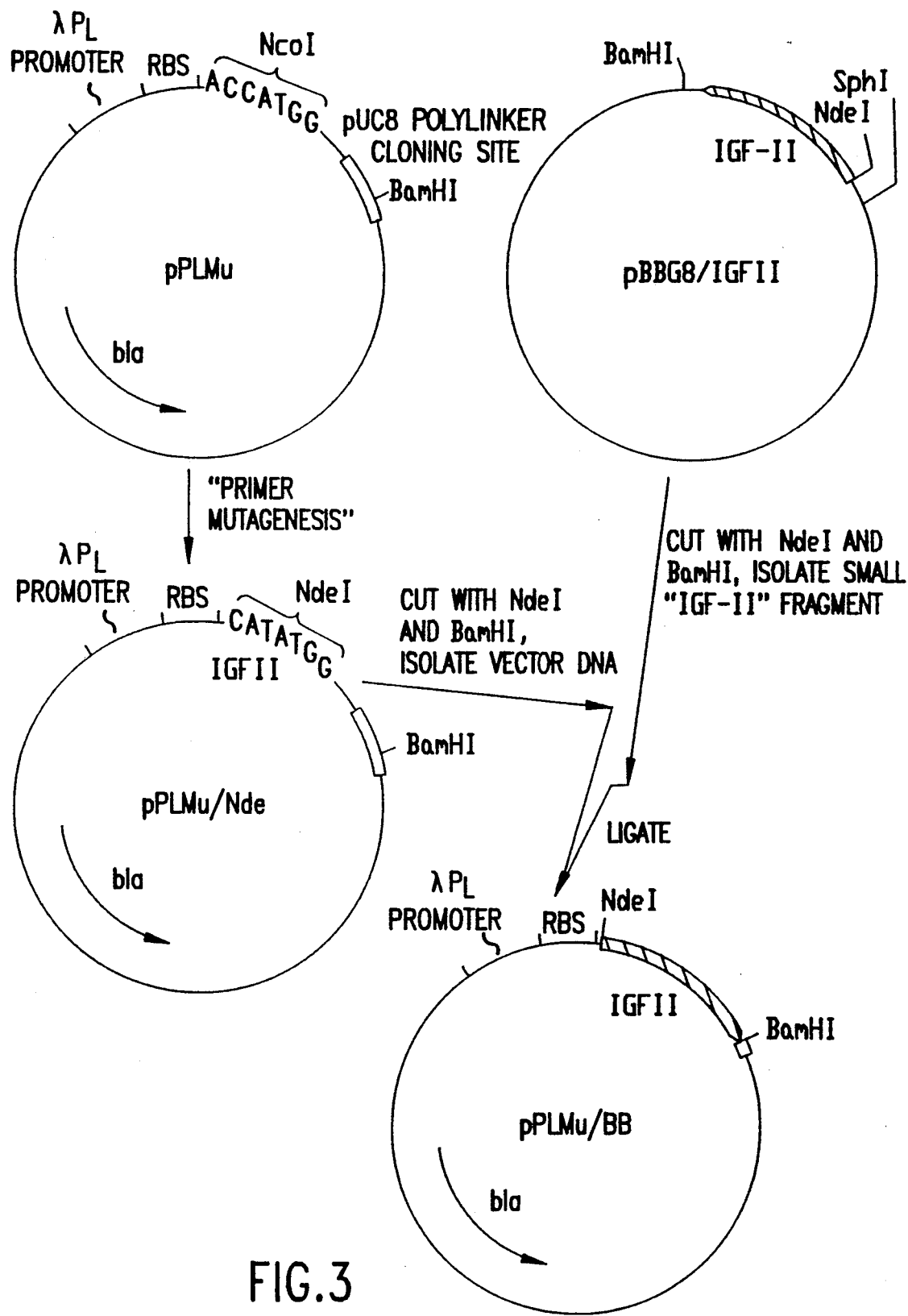

FIG. 3: Scheme of the cloning strategy for the construction of plasmid PLMu/BB.

Figure 4A:
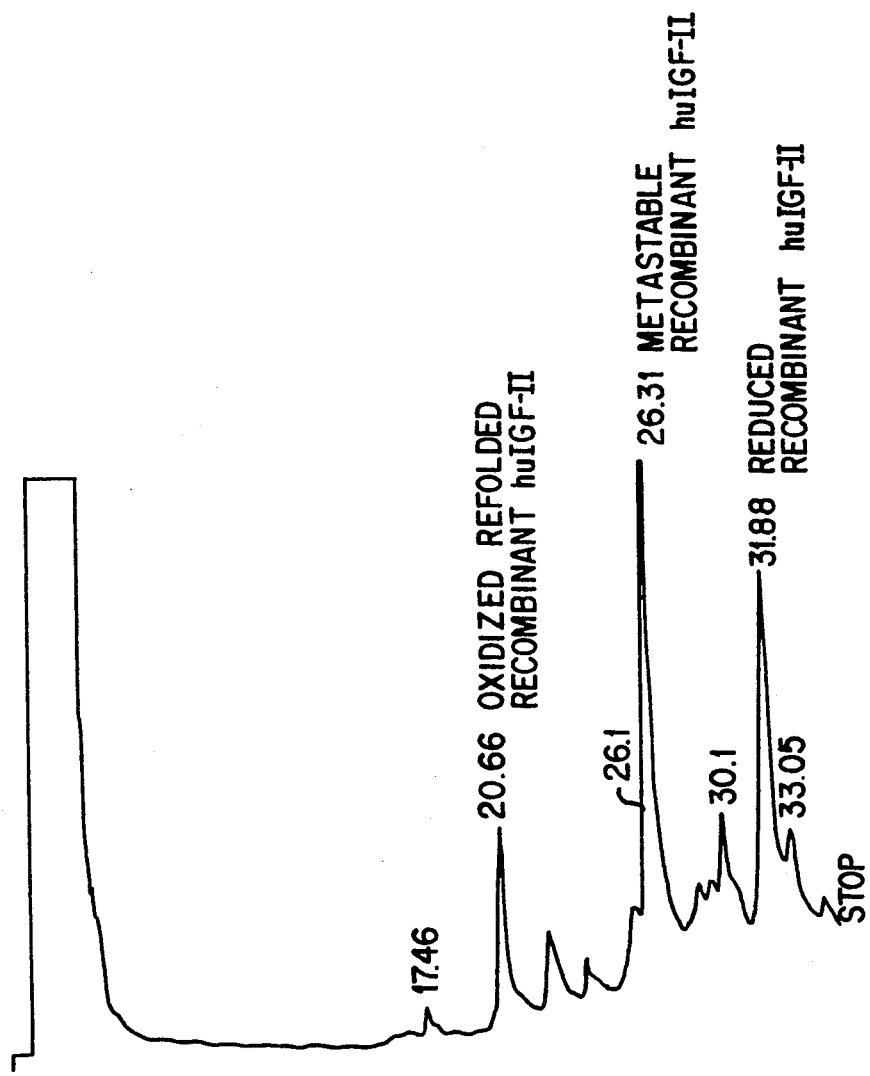

FIG. 4: Elution profiles of HPLC analysis of recombinant huIGF-II before (A) and after (B) refolding.

The following examples serve to illustrate the present invention, however are in no way intended to restrict it.

MATERIALS AND METHODS

Bacterial strains (*E. coli* K12)

LC 137: htpR$_{am}$, lon$_{R9}$, lac$_{am}$, mal$_{am}$, trp$_{am}$, pho$_{am}$, rpsL, tsx::Tn10, supC$_{ts}$ strain obtained from HARVARD UNIVERSITY; Goff, S. A. et al., PNAS (1984) 81, 6647–6651.

W 3110: λlysogen, hsdR

Plasmids pPLMu: Obtained from BIOGEN (Buell, g. et al., Nucl. Acids Res. (1985) 13, 1923–1938). This plasmid carried the bacteriophage λP$_L$ promoter with the phage Mu ner gene ribosome binding site (Van Leerdam, E. et al., Virology (1982) 123, 19–28; see also SEQ ID NO. 4).

pcI$_{857}$: Plasmid encoding a thermolabil λCI$_{857}$ repressor (Remault, E. et al. Gene (1983) 22, 103–113). If confers resistance to kanamycin.

pIGFII/3: pBR325 with the synthetic huIGF-II gene disclosed in the European patent application 0 123 228 cloned into the single EcoRI site (see also SEQ ID NO. 3)

pBBG8/IGFII: Plasmid pUC18 with the synthetic huIGF-II gene disclosed in the PCT patent application WO 89/03423 (SEQ ID NO. 2; including sequence for N-terminal methionine) cloned between the SphI and the BamHI site.

SDS gel-electrophoresis

SDS gel-electrophoresis (SDS-PAGE) is done as described previously (Laemmli, U.K. Nature (1970)

227, 680–685) using the Miniprotean II cell from BIORAD and 1 mm thick 18% polyacrylamide gels.

Heat-induction 7 ml of LB in a culture tube containing 40 μg of ampicillin and kanamycin (LB/amp/kan) are inoculated with a single colony and incubated with shaking over night at 30° C. 5 ml of this over night culture are added to 15 ml of LB/amp/kan in a 100 ml erlenmeyer flask and the flask transferred to a 42° C. waterbath shaker. 2 ml samples are taken before transfer and then 1 ml samples at 1 hr intervals up to 5 hrs. Cells are pelleted by centrifugation (5 min. at 10,000 rpm in Eppendorf® tubes and in an Eppendorf® centrifuge mod. 5415), the supernatant is discarded, the pellet then resuspended in 100 μl of sample buffer for SDS-gels and heated for 10 minutes at 95° C. 10 μl aliquotes are loaded for SDS-PAGE.

'Western' analysis

Proteins are transferred electrophoretically (Miniprotean II cell from BIORAD) to a membrane ('Immobilon' from MILLIPORE) using 0.7 A for 30 minutes in transfer buffer (25 mM Tris-base/192 mM glycine, 15% methanol) at room temperature. Blocking is done for 1 hr at room temperature with shaking in TBS (10 mM Tris-HCl, pH 7.2 at room temperature, 0.15M NaCl) containing 20% inactivated goat serum (GIBCO, cat. no. 063-6210, the serum is heat inactivated by incubation for 1 h in a 57° C. water bath). The membrane is then washed 3 times with 50 ml of TBS and incubated over night at 4° C. with a 1:2,000 dilution in TBS of rabbit anti-huIGF-II antiserum. The following manipulations are done at room-temperature. The membrane is then washed with 50 ml TBS for 15 min (repeat wash 2 more times). Immunoreactive proteins are visualized using a BIORAD kit (catalog no. 170-6509, 1987). The membrane is incubated for 1 h in 20 ml TBS with a 1:2,000 dilution of alkaline phosphatase conjugated goat anti-rabbit IgG, then washed 3 times as described above. For the following reaction the membrane is incubated in 15 ml of a solution containing: 66 μl of NBT (BIORAD catalog no. 170-6539, 75 mg/ml in 70% dimethyl formamide) and 50 μl of BCIP (BIORAD catalog no. 170-6532, 50 mg/ml in destilled water). The development of visible bands is followed and the reaction stopped by incubating the membrane in 50 ml of a 50 mM ethylendiamine tetraacetic acid (EDTA) solution (repeat 2 times).

Purification of DNA Fragments and Vector DNA

5 μg of plasmid DNA are cut to completion with restriction enzyme(s) following the recommendations of the supplier in 50 μl of buffer. The DNA is then precipitated by addition of 5 μl 3M sodium-acetate, 100 mM MgCl$_2$, 5 mM EDTA and 150 μl of ethanol. After 15 min incubation at −70° C. the DNA is pelleted by centrifugation at 13,000 g for 15 min. The supernatant is discarded and the DNA pellet resuspended in 80 μl 0.089M Tris-borate, 0.089M boric acid and 0.002M EDTA (TBE buffer) containing 0.25% bromphenol blue and 0.25% xylene cyanol. 4 times 20 μl samples are electrophoresed through a 1% agarose gel in TBS containing 0.5 μg/ml of ethidium bromide at 50 V till the bromphenol blue marker reached the bottom of the 10 cm long and 0.8 cm thick gel. The DNA band is visualized under short wave UV light, cut out with a razor blade and electro-eluted from the gel piece in the SCHLEICHER & SCHUELL 'BIOTRAP' apparatus applying 200 A for 1.5 h. The eluted DNA is precipitated (see above), resuspended in 20 μl TE (10 mM Tris-HCl pH 7.4 at room temperature, 1 mM EDTA) and used for further experiments.

Ligation of DNA fragments 10 ng of linearized and purified vector DNA and 3 times the molar equivalent of purified fragment DNA are incubated at 4° C. for 15 h in 20 μl of ligation buffer (70 mM Tris-HCl, pH 7.5 at 24° C., 10 mM MgCl$_2$, 5 mM dithiothreitol, 0.1 mM adenosine-triphosphate) containing 1 unit of DNA-ligase (Boehringer).

Transformation

10 μl of the ligation mixture obtained in the ligation of DNA fragments (see above) are added to 200 μl of cold (4° C.) competent E. coli cells (see below). Following 30 min. incubation the cells are heat shocked by incubation for 1.5 min in a 42° C. waterbath. 2 ml of LB are added and the culture shaked for 40 min in a 37° C. shaker in culture tubes. 200 μl aliquots are then plated onto LB plates containing 40 μg/ml of the appropriate antibiotics for selection.

Plasmid Preparation

Plasmid DNA is prepared according to the method of Birnboim, H. C. and Doly, J. (1979) Nuclei Acids Res., 7, 1513.

Preparation of Competent Cells

Competent E. coli cells are prepared by the calcium chloride procedure as described in: Maniatis, T. Fritsch, E. F. and Sambrook, J. 1982. Molecular Cloning (Cold Spring Harbor Laboratory, New York), pp. 250–251.

EXAMPLES

1. Preparation of plasmid PLMu/IGFII and expression of a huIGF-II gene in E. coli The huIGF-II gene as contained in pIGFII/3 (SEQ ID NO. 3) is cloned into pPLMu as shown in FIG. 1. The IGF-II gene in pPLMu/3 lacks a stop codon. This is reconstituted in pPLMu/IGFII by replacing the SalI-BamHI ('filled-in') fragment in pPLMu/3 by the SalI-PvuII fragment from pIGFII/3.

For expression studies plasmid PLMu/IGFII is transformed into the E. coli strain LC137 carrying the compatible plasmid pcI$_{857}$ and plated on LB-plates containing 40 μg/ml of ampicillin and kanamycin. Single colonies of fresh transformants are used for the heat-induction. The analysis by SDS-PAGE and coomassie brilliant blue staining is shown in FIG. 2A. Recombinant huIGF-II accumulates as inclusion bodies in the E. coli cells during the heat-induction, which was performed as described hereinbefore, to about 5–8% of whole cell protein. The identify of rIGF-II is demonstrated by a 'western' analysis with rabbit anti-huIGF-II antibodies as shown in FIG. 2B. Furthermore the heat induced protein band with the apparent molecular weight of 7500 d is cut out of the gel and subjected to N-terminal amino acid analysis. The sequence thus obtained reads A-Y-R-P-S-E-T-L-?-G-G-E-L-V-D-T-L-Q (in position "?" the amino acid is not determined) and corresponds to the one of natural huIGF-II. The meaning of the single letter code for the amino acids is given above.

2. Preparation of plasmid PLMu/BB and expression of a huIGF-II gene in E. coli

The huIGF-II gene with the DNA sequence with SEQ ID NO. 2 was cloned into the expression vector pPLMu/Nde as shown in FIG. 3. Plasmid pPLMu/Nde was prepared as follows:

Plasmid pPLMu was cut at the single site with the restriction endonuclease NdeI. The 5'-overhanging ends were made blunt-ended using "Klenow"-DNA polymerase, 2'-deoxyadenosine-5'-triphosphate and thymidine-5'-triphosphat and ligated as described by T. Maniatis, E. F. Fritsch and J. Sambrook (1982) in "Molecular Cloning", Cold Spring Harbor Laboratory, resulting in plasmid pPLMu/Nonde. The NcoI site in pPLMu/Nonde was converted to a NdeI site using a commercial kit for oligonucleotide-directed in vitro mutagenesis (Amersham, code RPN. 2322) and the primer 5'-CGTAACCATATGAAAAACCC resulting in plasmid pPLMu/Nde. Expression studies with plasmid PLMu/BB in $E.\ coli$ LC137/pcT$_{857}$ showed similar expression levels of recombinant huIGF-II as with pPLMu/IGFII.

3. Isolation of inclusion bodies comprising recombinant huIGF-II from $E.\ coli$ LC137 transformed with plasmid PLMu/IGFII Cells induced according to example 1 are separated and washed twice in breaking buffer (50 mM Tris-HCl, 10 mM EDTA, pH 7.0) and sonificated for 10 min and centrifuged (30 min. 13,000 g, 4° C.). The pellet comprises the inclusion bodies.

4. Solubilization of the inclusion bodies with buffer containing urea

Inclusion bodies obtained according to example 3 are resuspended in a solubilization buffer (8M urea, 100 mM Tris-HCl, 8 mM EDTA, 5 mM Benzamidine, 5 mM DTT, pH 6.5), sonificated for 2-5 min and centrifuged (30 min, 13,000 g, 4° C.). The supernatant comprises unfolded recombinant huIGF-II.

5. Solubilization of the inclusion bodies with acetic acid

Inclusion bodies obtained according to example 3 are solubilized in a 70% (v/v) aqueous acetic acid.

6. Purification of recombinant huIGF-II prior to refolding

The supernatant obtained according to example 4 is applied on a gel filtration column (Sephacryl S-200) before folding. The equilibration and elution buffer contains 8M urea, 100 mM Tris-HCl, 10 mM DTT at pH 6.5

Fractions eluting from the Sephacryl S-200 column are analysed on SDS-PAGE and the fractions which contain recombinant huIGFII are pooled for further processing.

7. Refolding of recombinant huIGF-II

Figure 4B:
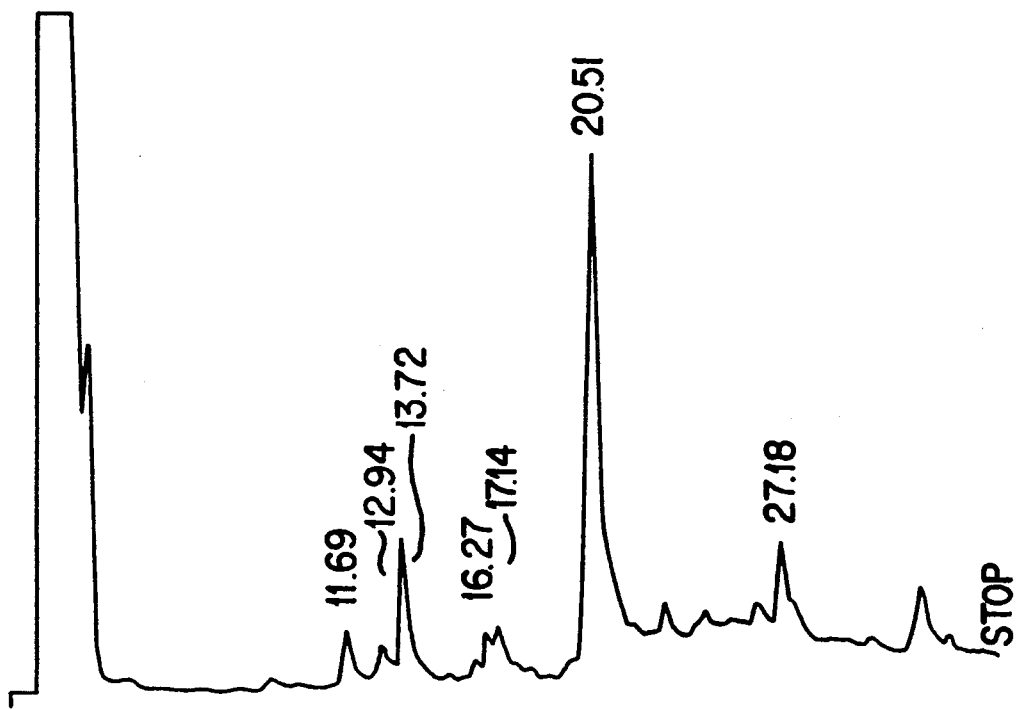

Refolded recombinant huIGF-II is obtained from the pool obtained according to example 6 or from the supernatant obtained according to example 4 by dialyzing it against folding buffer (50 mM Tris-HCl, 4 mM DTT, 1.5 mM L-Cystin, 4.5 mM L-Cystein, pH 8.5) at 4° C. under oxygen free conditions obtained by degassing with Argon until the urea concentration is 2M and by subsequently incubating this reaction mixture for 24 h at 30° C. The refolding is monitored by reverse phase HPLC of samples of the reaction mixture taken at the beginning of the incubation at 30° C. (FIG. 4A) and after 18 h (FIG. 4B).

8. Reverse Phase HPLC of recombinant huIGF-II

Separation of unfolded (reduced, metastable and refolded (oxidized) recombinant huIGF-II is achieved by treatment with acetic acid at pH 3 and concomittent chromatography of the supernatant on reversed phase HPLC. The results are shown in FIG. 8. Experimental conditions: Equipment: Kontron. Column: Vydac C18 5 μm, Stationary phase: 218 TP 5415. Aliquot portions: 600 μl. Flow rate: 1.2 ml/min. Eluent A: 0.1% trifluoroacetic acid. Eluent B: Acetonitrile/water 8:2+0.08% trifluoroacetic acid. Pressure: ca. 100 bar. Abs. at 216 nm.

9. Characterization of recombinant huIGF-II

Fraction 1 at 20.66 (FIG. 4A) or 20.51 (FIG. 4B) (peak is in FIG. 4 indicated as "oxidized refolded") isolated by HPLC according to example 8 is characterized as follows:

a) Determination of the amino acid composition of recombinant huIGF-II

Recombinant huIGF-II isolated from fraction 1 of the HPLC eluate is hydrolyzed with HCl and then analysed as described in Chang et al. in Methods in Enzymology 91: 41 (1983). The hydrolysate has the amino acid composition given in Table 1.

TABLE 1 amino acid composition of recombinant huIGF-II from $E.\ coli$
Values in brackets represent the numbers of the amino acids
in the amino acid sequence shown under SEQ ID NO. 1.

| Amino Acid | Hydrolysate |
|---|---|
| Asx | 3.3 (3) |
| Thr | 3.8 (4) |
| Ser | 7.6 (7) |
| Glx | 6.3 (7) |
| Pro | 3.6 (3) |
| Gly | 6.3 (5) |
| Val | 4.0 (4) |
| Ala | 4.8 (5) |
| Cystein | 5.0 (6) |
| Ile | 0.5 (1) |
| Leu | 5.5 (6) |
| Tyr | 1.2 (3) |
| Phe | 4.3 (4) |
| His | — (—) |
| Lys | 1.2 (1) |
| Arg | 8.3 (8) |
| Met | — (—) |
| Total | 67 | b) Partial sequence analysis

Approximately 35 μg of recombinant huIGF-II isolated from fraction 1 of the HPLC eluate are subjected to a conventional sequence analysis according to Edman and the N-terminal phenylthiohydantoin amino acids are determined by means of reverse phase HPLC. Results of 35 cycles are Cycle      1                   10                    20
Amino acid A Y R P S E T L - G G E L V D T L Q F V Cycle      21                  30         35
Amino acid - G D R G F Y F - R P A S R V c) Apparent molecular weight of recombinant huIGF-II Recombinant huIGF-II is analysed on a SDS Polyacrylamide gel according to Laemmli et al., Nature 227: 680–685 (1970) under reducing and non reducing conditions. Under both conditions an apparent molecular weight of about 7500 D is determined for recombinant huIGF-II.

d) Molecular weight determination by $^{252}$Cf-PD-mass spectrometry

5 μg rIGF-II dissolved in 10 μl of a 1:1 (v/v) mixture of water and acetic acid. The protein is adsorbed to a nitrocellulose coated sample holder and mass spectrum is recorded on a $^{252}$Cf plasma desorption time of flight mass spectrometer model Bioion 20 (BIO ION Nordic AB, Uppsala, Sweden) with a flight tube length of 13 cm.

The spectrum is collected at +19 kV accellerating potential. The determined mass weight of the m+H+ ions is 7469. The calculated molecular weight is 7469,5.

Deposition of Microorganisms

The following microorganisms were deposited on Nov. 14, 1989 under the Budapest Treaty with Deutsche Sammlung von Mikroorganismen, Mascheroder Weg 1b, D-3300 Braunschweig:

Escherichia coli LC137 transformed with pcI$_{857}$ and pPLMu/BB was deposited as LC137/BB under No. DSM5641.

Escherichia coli LC137 transformed with pcI$_{857}$ and pPLMu/IGFII was deposited as LC137/IGFII under No. DSM5642.

---

We claim:

1. A process for the production of a recombinant IGF-II without a covalently attached foreign protein moiety and without N-terminal attached methionine or a derivative of methionine, said process comprising:
   a) transforming a suitable strain of *E. coli*, said strain being a lon⁻ and htpR⁻ double mutant, with a hybrid vector comprising an expression cassette consisting of the following elements in the 5' to 3' direction, said elements which are operably linked: an inducible promoter, a ribosomal binding site, and the codon for the amino acid methionine linked in proper reading frame to a DNA sequence encoding a human IGF-II having the amino acid sequence of SEQ ID NO. 1,
   b) culturing said transformed strain under conditions suitable for production of a recombinant IGF-II from said expression cassette.

2. A process according to claim 1 in which the host strain is *E. coli* LC137.

3. A process according to claim 1 in which the promoter of the expression cassette is tightly regulated.

4. A process according to claim 3 wherein the promoter of the expression cassette is the $P_L$ promoter and the strain of *E. coli* additionally comprises a DNA sequence encoding a protein regulating the $P_L$ promoter, wherein said protein regulating the promoter is encoded by the $cI_{857}$ repressor gene.

5. A process according to claim 1 wherein the DNA sequence encoding an IGF-II consists essentially of the sequence SEQ ID NO. 2.

6. A process according to claim 1 wherein the DNA sequence encoding an IGF-II consists essentially of the sequence SEQ ID NO. 3.

7. A process according to claim 1 in which the ribosomal binding site is the phage Mu ner gene ribosomal binding site of SEQ ID NO. 4.

8. A process according to claim 1 in which the hybrid vector is pPLMu/BB.

9. A process according to claim 1 in which the hybrid vector is pPLMu/IGFII.

10. A hybrid vector comprising an expression cassette consisting of the following elements in the 5' to 3' direction, said elements which are operably linked: an inducible promoter, a ribosomal binding site, and the codon for the amino acid methionine linked in the proper reading frame to a DNA sequence encoding a human IGF-II having the amino acid sequence of Seq. ID No. 1.

11. A hybrid vector according to claim 10 which is pPLMu/BB.

12. A hybrid vector according to claim 10 which is pPLMu/IGFII.

13. A transformed host cell which is an *E. coli* strain, said strain being a lon$^-$ and htpR double mutant, transformed with the hybrid vector of claim 10.

14. A transformed host cell according to claim 13 which is *E. coli* LC137 transformed with pPLMu/IGFII and pcI$_{857}$.

15. A transformed host cell according to claim 13 which is *E. coli* LC137 transformed with pPLMu/BB and pcI$_{857}$.

* * * * *